US011274177B2

(12) United States Patent
Kobilka et al.

(10) Patent No.: US 11,274,177 B2
(45) Date of Patent: Mar. 15, 2022

(54) TERMINALLY-FUNCTIONALIZED CASHEW NUT SHELL LIQUID DERIVATIVES

(71) Applicant: International Business Machines Corporation, Armonk, NY (US)

(72) Inventors: Brandon M. Kobilka, Tucson, AZ (US); Jacob Porter, Highland, NY (US); Jason T. Wertz, Pleasant Valley, NY (US); Scott B. King, Rochester, MN (US)

(73) Assignee: International Business Machines Corporation, Armonk, NY (US)

( * ) Notice: Subject to any disclaimer, the term of this patent is extended or adjusted under 35 U.S.C. 154(b) by 258 days.

(21) Appl. No.: 16/411,422

(22) Filed: May 14, 2019

(65) Prior Publication Data

US 2020/0362087 A1    Nov. 19, 2020

(51) Int. Cl.
| | | |
|---|---|---|
| *C08G 18/32* | (2006.01) | |
| *C08G 63/20* | (2006.01) | |
| *C07C 37/00* | (2006.01) | |
| *C07C 39/11* | (2006.01) | |
| *C08G 18/76* | (2006.01) | |
| *C08G 63/133* | (2006.01) | |
| *C08G 63/06* | (2006.01) | |
| *C08G 63/127* | (2006.01) | |

(52) U.S. Cl.
CPC ......... *C08G 18/3215* (2013.01); *C07C 37/00* (2013.01); *C07C 37/002* (2013.01); *C07C 39/11* (2013.01); *C08G 18/7621* (2013.01); *C08G 63/065* (2013.01); *C08G 63/127* (2013.01); *C08G 63/133* (2013.01); *C08G 63/20* (2013.01); *C08G 2110/0008* (2021.01); *C08G 2110/0025* (2021.01)

(58) Field of Classification Search
CPC ............... C08G 18/3215; C08G 63/20; C08G 2110/0008; C08G 2110/0025; C08G 18/7621; C08G 63/133; C08G 63/065; C08G 63/127; C07C 37/002; C07C 39/11; C07C 37/00
See application file for complete search history.

(56) References Cited

U.S. PATENT DOCUMENTS

| | | | |
|---|---|---|---|
| 7,244,772 B2 | 7/2007 | Ittara et al. | |
| 9,035,105 B2 | 5/2015 | Reese et al. | |
| 9,732,181 B2 | 8/2017 | King et al. | |
| 9,796,802 B2 | 10/2017 | Pinto et al. | |
| 10,023,763 B2 | 7/2018 | Watkins et al. | |
| 2011/0315591 A1* | 12/2011 | Lespinasse | C09D 167/00 206/524.3 |
| 2017/0247496 A1 | 8/2017 | Wang et al. | |
| 2017/0313806 A1 | 11/2017 | Yu et al. | |
| 2017/0349812 A1* | 12/2017 | Gupta | C09K 8/5756 |

FOREIGN PATENT DOCUMENTS

WO    WO-2011003446 A1 *    1/2011    ............. C07C 39/16

OTHER PUBLICATIONS

Sakulsaknimitr et al., "Structure and Thermal Properties of Polyurethanes Synthensized from Cardanol Diol," J Polym Environ (2015) 23: 216-226, Springer. DOI: 10.1007/sl 0924-014-0707-2.
Waitara, F.N., "Evaluation of Cashew Nut Shell Liquid Based Products as Reactive Diluents for Alkyd Coatings," Thesis, 2015, 79 pages.
Hess et al., "Valorization of Unconventional lipids from microalgae or tall oil via a selective dual catalysis one-pot approach," Supporting Information, Journal of the American Chemical Socity, 139(38), Sep. 2017, 15 pages.
Witt et al., "Unsymmetrical α,ω-Difunctionalized Long-Chain Compounds via Full Molecular Incorporation of Fatty Acids," ACS Catalysis, 2015, 5, pp. 4519-4529, ACS Publications. DOI: 10.1021/acscatal.5b00825.
Hanna et al., "Primary and secondary hydroxyl group content of polypropylene glycols," Journal of Polymer Science banner, vol. 56, Issue 164, Feb. 1962, pp. 297-304, Wiley Online Library. (Abstract Only) https://onlinelibrary.wiley.com/doi/abs/10.1002/pol.1962.1205616402.
Zlatanic et al., "Structure and Properties of Triolein-Based Polyurethane Networks," Bio Macromolecules, 2002, 3(5), pp. 1048-1056, American Chemical Society. (Abstract Only) DOI: 10.1021/bm020046f.
"Innovation Award "Bio-based Material of the Year 2018" goes to Arctic Biomaterials from Finland for degradable glass fibre reinforced PLA," Bio-based News, May 17, 2018, 3 pages. http://news.bio-based.eu/innovation-award-bio-based-material-of-the-year-2018-goes-to-arctic-biomaterials-from-finland-for-degradable-glass-fibre-reinforced-pla/.
"CNSL Polyols and Diols," Cardolite—Chemistry for Tomorrow, printed Apr. 2, 2019, 2 pages. https://www.cardolite.com/technology/polyols_diols/.
Augustin et al., "Conversion of oleic acid to 17- and 18-substituted stearic acid derivatives by way of the "acetylene zipper"," European Journal of Organic Chemistry, vol. 1991, Issue 10, pp. 1037-1040. (Abstract Only).
Augustin et al., "Alkynic fatty acids: ω-Arylation, methoxycarbonylation to α,β-unsaturated esters, cyclotrimerization to pyridines and 2-pyridones," European Journal of Lipid Science and Technology, vol. 113, Issue 1, Jan. 2011, pp. 72-82. (Abstract Only).

\* cited by examiner

*Primary Examiner* — Rabon A Sergent
(74) *Attorney, Agent, or Firm* — Kelsey M. Skodje (57) ABSTRACT

A terminally-functionalized derivative of a cashew nut shell liquid (CNSL) compound, a method to form a polymer, and an article of manufacture comprising a polymer derived from the terminally-functionalized CNSL derivative. The terminally-functionalized CNSL derivative has two, three, four, or five reactive functional groups. The polymer is prepared by obtaining CNSL compounds, reacting the CNSL compounds to form the terminally-functionalized CNSL derivative, and polymerizing the terminally-functionalized CNSL derivative.

14 Claims, 10 Drawing Sheets

TERMINALLY-FUNCTIONALIZED CASHEW NUT SHELL LIQUID DERIVATIVES

BACKGROUND

The present disclosure relates to biorenewable polymer synthesis and, more specifically, to forming polymers from derivatives of cashew nut shell liquid (CNSL) compounds.

Polyol compounds are compounds with at least two hydroxyl groups. Polyols and other functionalized compounds can be derived from petrochemical or biorenewable sources, such as various plant oils and CNSL. These compounds can be used to form polymers. For example, polyols can be reacted with isocyanates to form polyurethanes. When blowing agents are incorporated into these reactions, polyurethane foams can be produced. Polyurethane foams are used in a variety of applications, such as thermal insulation and acoustic dampening.

SUMMARY

Various embodiments are directed to a compound having the structure:

where Q and Q' are reactive functional groups, and R and R" are either reactive functional groups or hydrogen atoms. When R" is a reactive functional group, R' is either a reactive functional group or a hydrogen atom, and when R" is a hydrogen atom, R' is also a hydrogen atom. The reactive functional groups can be hydroxyl or epoxy groups. In some embodiments, Q' is a vinyl group. In some embodiments, each of Q, Q', R, R', and R" is a hydroxyl group.

Additional embodiments are directed to a method, which includes obtaining cashew nutshell liquid (CNSL) compounds, reacting the CNSL compounds to form terminally-functionalized CNSL derivatives, and polymerizing the terminally-functionalized CNSL derivatives. The terminally-functionalized CNSL derivatives can be terminal polyol CNSL derivatives, which can be polymerized in a reaction with a diisocyanate. The polymerization can include adding a blowing agent. Further, the polymerization can include forming a mixture containing the terminally-functionalized CNSL derivatives, such as the terminal polyol CNSL derivatives, and at least one monomer from a non-CNSL source, such as a petroleum-derived polyol. In some embodiments, the reacting CNSL compounds includes converting sidechain alkene moieties on the CNSL compounds to alkyne moieties to form alkyne CNSL derivatives, reacting the alkyne CNSL derivatives with a base to form terminal alkyne CNSL derivatives, and hydroxylating the terminal alkyne CNSL derivatives to form terminal polyol CNSL derivatives. The method can also include reacting the terminally-functionalized CNSL derivative with epichlorohydrin to form an epoxy resin.

Further embodiments are directed to an article of manufacture that includes a polymer. The polymer has a number (n) of repeat units derived from at least one terminally-functionalized cashew nutshell liquid (CNSL) derivative. The at least one terminally-functionalized CNSL derivative has two, three, four, or five reactive functional groups. In some embodiments, the polymer is a polyurethane or a polyester. The polymer can also be a foam. Further, at least 5% by weight of the polymer can be derived from the at least one terminally-functionalized CNSL derivative.

DETAILED DESCRIPTION

Cashew nut shell liquid (CNSL) is a by-product of cashew nut processing. CNSL contains a mixture of compounds, which can include phenolic lipids such as anacardic acid, cardol, 2-methylcardol, and cardanol. Herein, the term "CNSL compounds" refers to any these phenolic lipids, alone or in combination, unless otherwise specified. The alkyl sidechains on the CNSL compounds typically have fifteen carbon atoms (C15), and can be saturated or unsaturated with between one and three carbon-carbon double bonds (alkene moieties). There can be alkyl sidechains with seventeen carbon atoms (C17) as well, though these are not illustrated herein. Reactions involving these alkene moieties can be carried out in order to derive various compounds. Compounds derived from the CNSL compounds are referred to herein as "CNSL derivatives".

Hydroxylation of CNSL compound sidechains produces polyol CNSL derivatives, which can include diols, triols, and/or polyols having four or more hydroxyl groups. The polyol CNSL derivatives can be reacted further to provide additional functionalities (e.g., epoxy or acetate groups) and/or form polymers. For example, polyol CNSL derivatives can be reacted with epichlorohydrin to form epoxy resins. Further, polyol CNSL derivatives can be reacted with isocyanates to form polyurethanes. Polyol CNSL derivatives can also be reacted with isophthalates, dicarboxylic acids and their esters, or acid chlorides to form polyesters. Various additional polymers that can be formed from CNSL derivatives can include polyamides, poly(vinyl-esters), polyacrylates, polycarbonates, polyhydroxyurethanes, etc.

Because of their versatile polymer applications, CNSL derivatives can be used to form materials that were previously produced from non-renewable hydrocarbons (e.g., polyols derived from petrochemicals). For example, foams (e.g., polyurethane foams) can be produced by using blowing agents to introduce air into the polymerization of polyol CNSL derivatives and optional co-monomers (e.g., isocyanates). Additional examples of materials that can be made from CNSL-derived polymers can include plastics, paints, coatings, adhesives, synthetic fibers, insulation, and synthetic rubbers. Polyol CNSL derivatives provide advantageous properties to polymers, such as hydrophobicity for improved water resistance. Further, polyol CNSL derivatives can provide reduced moisture sensitivity during the formation of polyurethane. This results in increased durability of the polyurethane.

There are also advantages to increasing biorenewable content in polyurethanes and other polymers. For example, there is greater variety in the reactivity and other properties of compounds available from biological sources than from petrochemical sources. Therefore, using biorenewable sources enables the production of more diverse materials with tunable properties. Further, using biorenewable polyols conserves the Earth's supply of petroleum, which is a non-renewable resource. Biorenewable polyols can also be obtained with less energy expenditure than petrochemical-derived polyols (e.g., without the drilling, extraction, refining, and processing required to produce polyols from petrochemicals).

However, polyols derived from lipid sources such as CNSL and vegetable oil can have disadvantages caused by structural features (e.g., low ratios of primary to secondary hydroxyl groups and cross-linking in the middles of alkyl sidechains). These disadvantages can include reduced cross-linking density and disruptions in polymer network structures caused by large numbers of terminal alkyl chains ("dangling chains"). Therefore, biorenewable lipid-derived polyols are typically blended with petrochemical-derived polyols to limit the effects of the dangling chains. Because of the aforementioned disadvantages, the biorenewable content is generally very low in polyurethanes (e.g., less than about 10%) and other polymers.

Disclosed herein are processes for forming CNSL derivatives with terminal functional groups and, consequently, no dangling chains. Instead, the CNSL derivative sidechains include hydroxyl or other reactive functional groups (moieties that participate in chemical reactions such as addition, substitution, elimination, polymerization, etc.) at terminal carbon atoms. The terminally-functionalized CNSL derivatives can be used to form polymers having improved mechanical properties. This provides an avenue for increasing the biorenewable content in polymers (e.g., where more than 5-10% of the total weight of a polymer is from terminally-functionalized CNSL derivatives).

The structures of the terminally-functionalized CNSL derivatives can be summarized by the following structure:

where Q and Q' are reactive functional groups, and R, R', and R" are independently either reactive functional groups or hydrogen atoms. The alkyl sidechain can be numbered so that the terminal carbon atom is C-15. Using this numbering system, R' is linked to C-11, R" is linked to C-13, and Q' is linked to C-15. A reactive functional group represented by Q', R', or R" can be a substituent (an atom or group of atoms replacing a hydrogen atom on the alkyl sidechain) or an unsaturated bond location. For example, Q' can represent a double or triple bond linking C-15 and C-14; R', a double or triple bond linking C-13 and C-12; and R", a double or triple bond linking C-11 and C-10. Examples of substituents can include hydroxyl, epoxy, propylene carbonate, and ester groups. In some embodiments, a substituent such as a carboxylic acid or methyl group is also attached to the benzene ring of a terminally-functionalized CNSL derivative. This is discussed in greater detail below.

Figure 1:
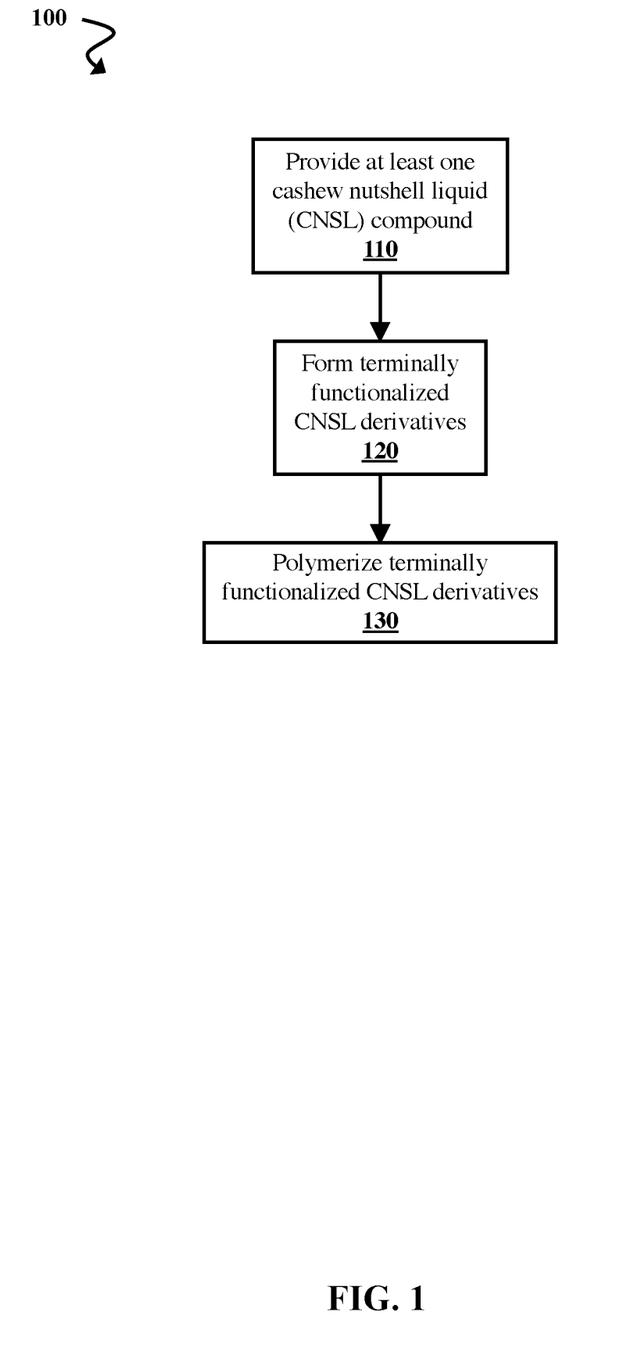
FIG. 1 is a flow diagram illustrating a process of forming cashew nut shell liquid (CNSL)-derived polymers.
Figure 2:
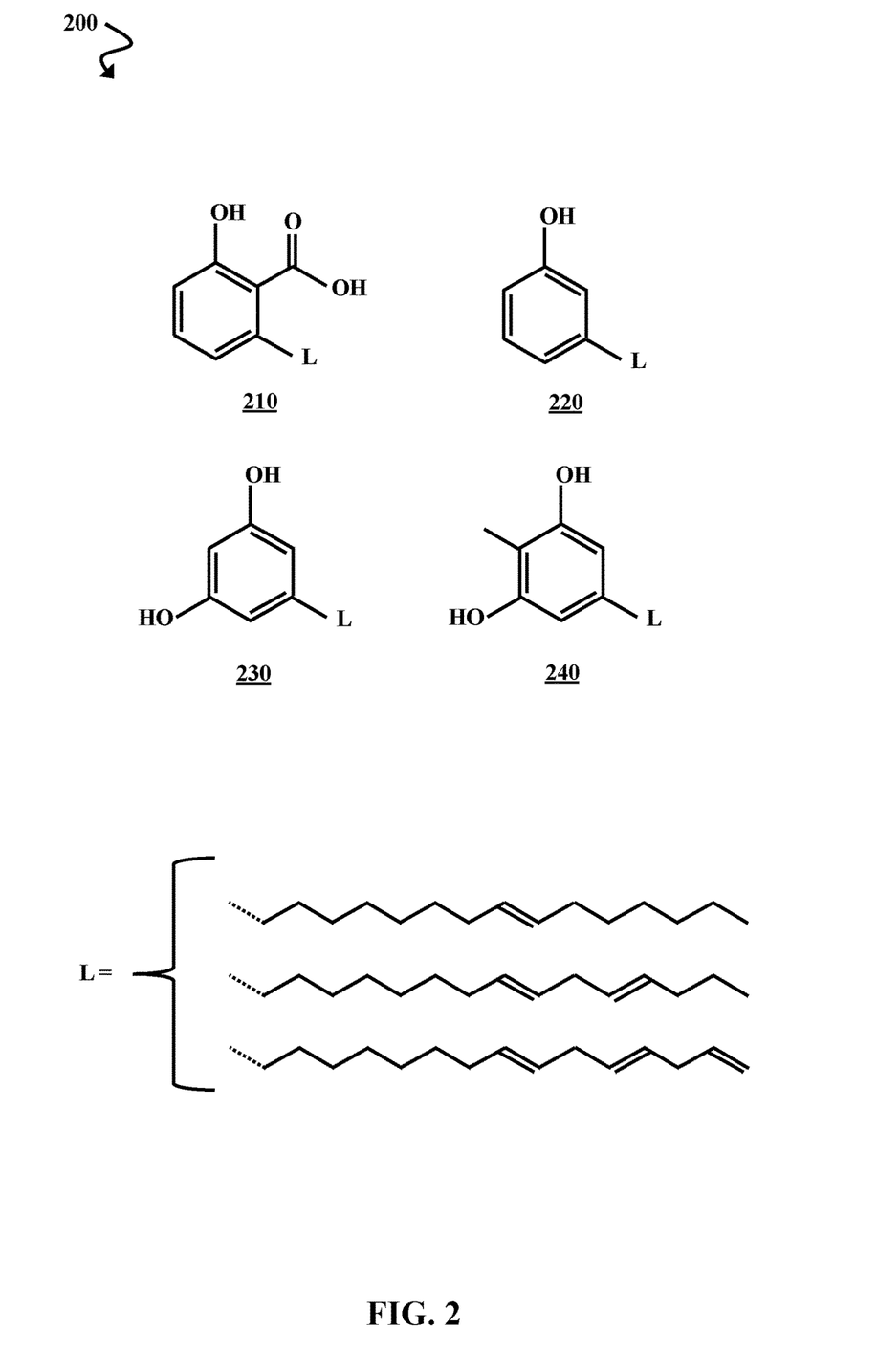
FIG. 2 is a chemical structure diagram illustrating examples of CNSL compounds, according to some embodiments of the present disclosure.

FIG. 1 is a flow diagram illustrating a process 100 of forming CNSL-derived polymers. Compounds from CNSL are provided. This is illustrated at step 110. The CNSL compounds are phenolic lipids that include at least one of anacardic acid, cardol, 2-methylcardol, and/or cardanol. Examples of these compounds are illustrated in FIG. 2. In addition to the phenolic lipid CNSL compounds, CNSL can also include components such as phytosterols and triacontanes. CNSL can be obtained as an extract (e.g., from a commercial source) or it can be extracted in situ (e.g., by extraction from cashew shells in hexane at room temperature). In some embodiments, CNSL is used without separating out any of its phenolic lipid components.

However, in other embodiments one or more CNSL compounds can be separated from the extracted liquid prior to forming CNSL derivatives. For example, cardanols can be extracted from CNSL by column chromatography or other separation techniques known to those of ordinary skill in the art. The cardanol content in CNSL can optionally be increased by converting anacardic acid to cardanol. For example, anacardic acid can be converted into cardanol by heating at about 150° C. for approximately four hours in the presence of calcium hydroxide ($Ca(OH)_2$). However, pre-isolated compounds can also be obtained (e.g., cardanol from a commercial source).

Figure 3:
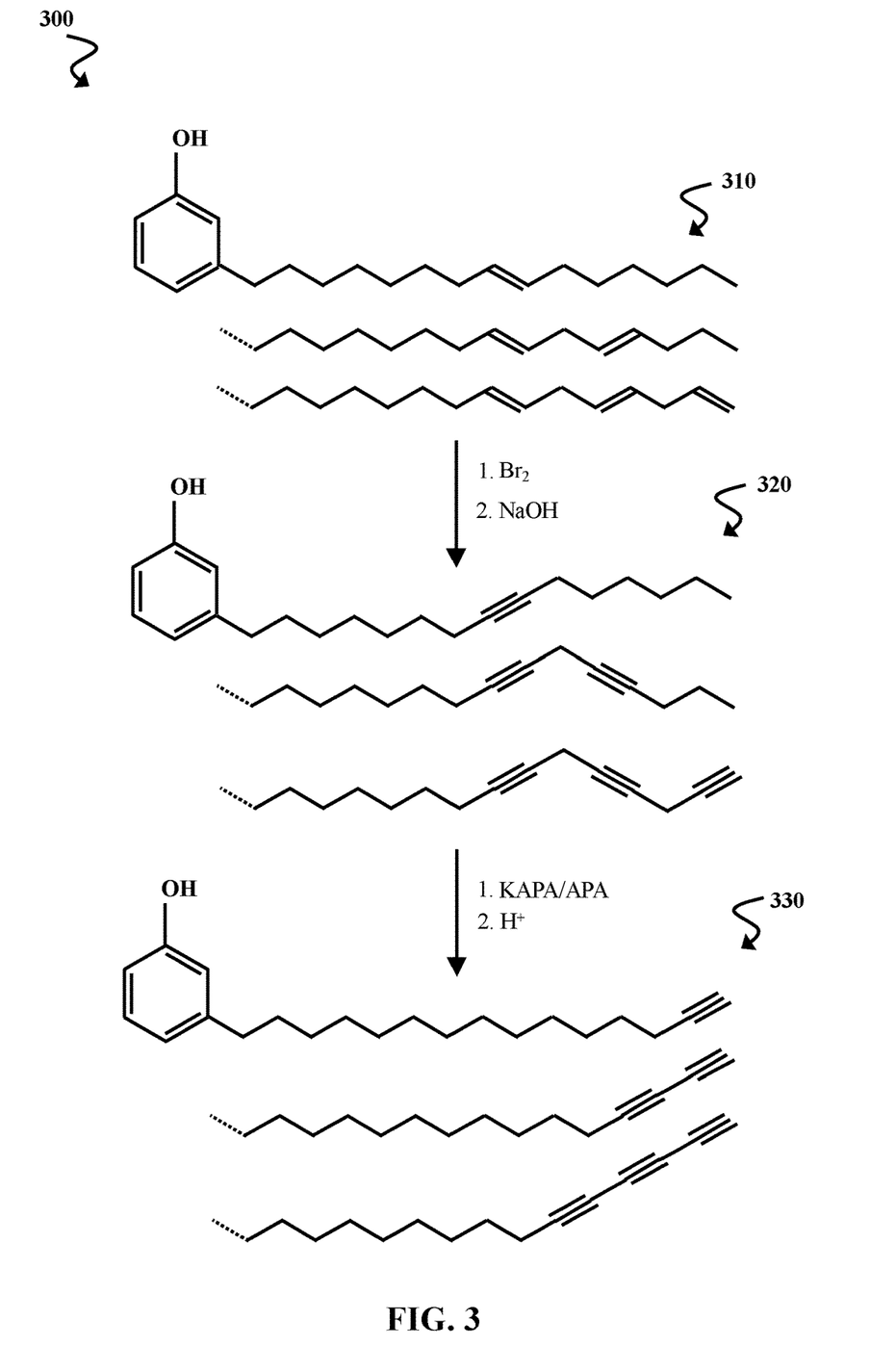
FIG. 3 is a chemical reaction diagram illustrating a process of forming terminal alkyne CNSL derivatives, according to some embodiments of the present disclosure.

The CNSL compounds are converted into terminally-functionalized CNSL derivatives. This is illustrated at step 120. In some embodiments, this step includes forming CNSL derivatives having terminal alkyne (—C≡CH) moieties. In these instances, double bonds on CNSL compound alkyl sidechains are dehydrogenated to form the alkyne moieties. The resulting alkyne CNSL derivatives are then isomerized (e.g., via alkyne zipper reactions) to form terminal alkyne moieties. Examples of terminal alkyne CNSL derivatives are illustrated in FIG. 3.

Figure 4A:
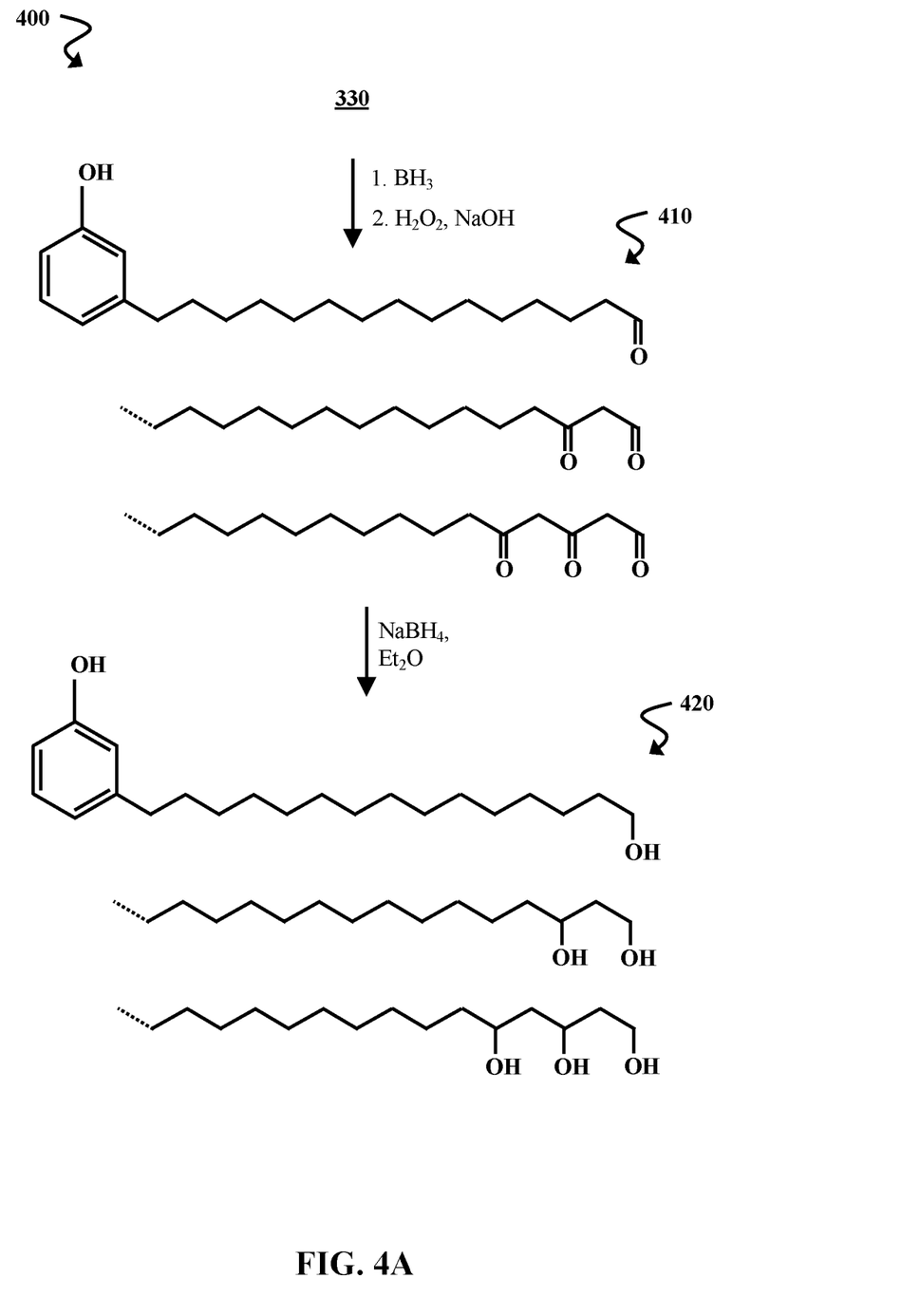
FIG. 4A is a chemical reaction diagram illustrating a process of forming terminal polyol CNSL derivatives, according to some embodiments of the present disclosure.
Figure 4B:
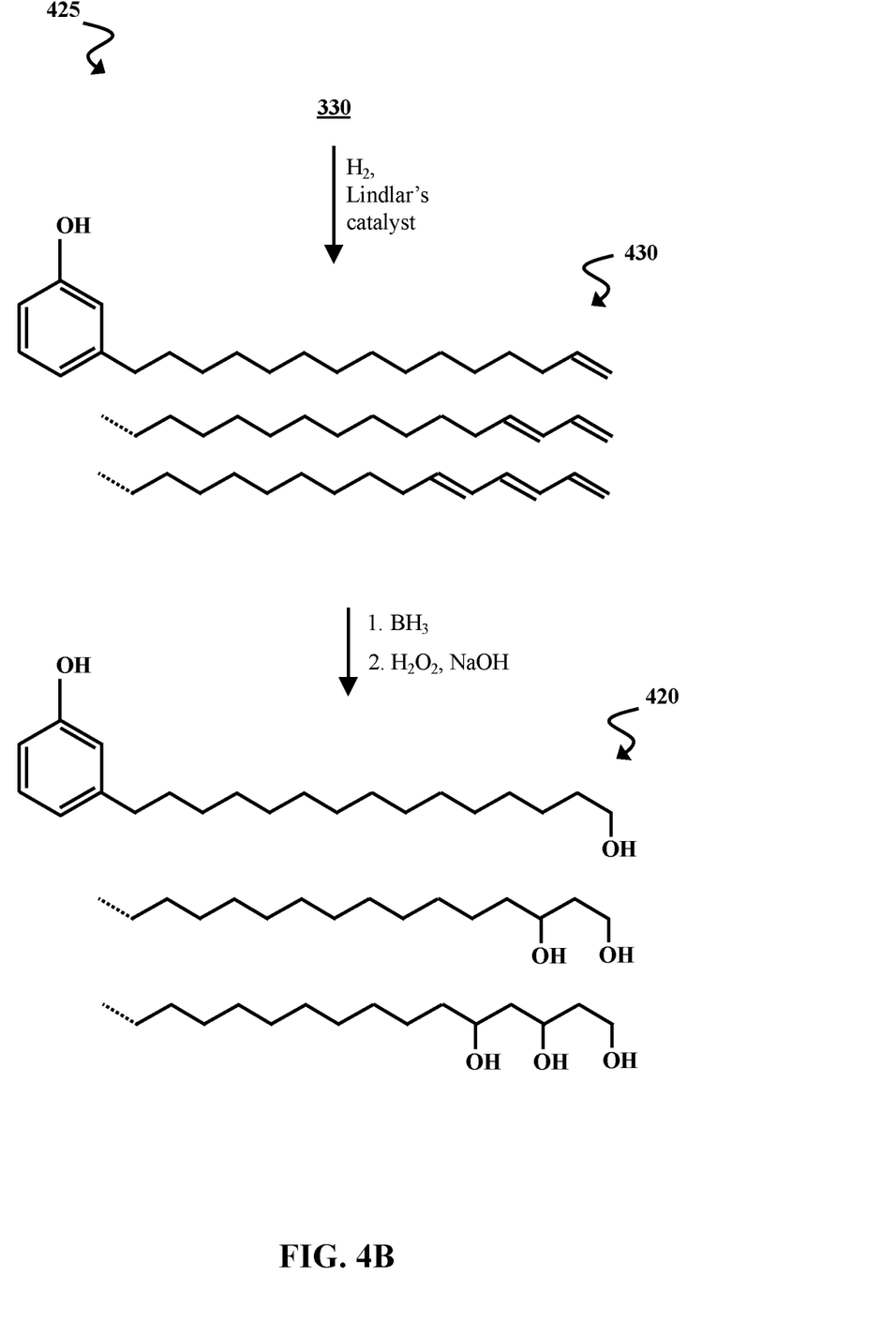
FIG. 4B is a chemical reaction diagram illustrating a second process of forming terminal polyol CNSL derivatives, according to some embodiments of the present disclosure.
Figure 5:
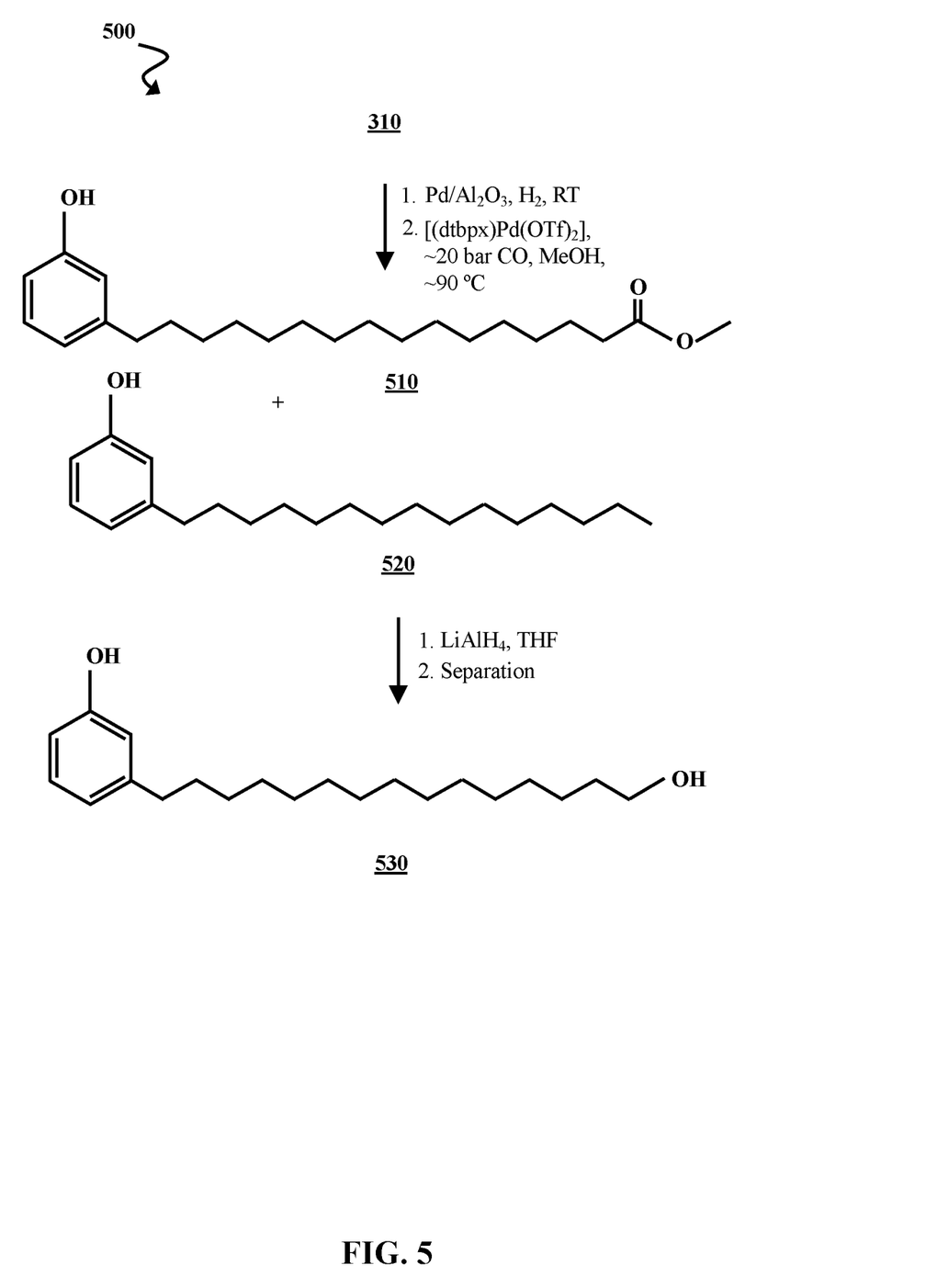
FIG. 5 is a chemical reaction diagram illustrating a third process of forming polyol CNSL derivatives, according to some embodiments of the present disclosure.

The terminal alkyne CNSL derivatives can then be reacted further to form terminal polyol CNSL derivatives. For example, the alkyne moieties can be converted into carbonyls by hydroboration-oxidation, followed by reduction to hydroxyls (e.g., by sodium borohydride). Alternatively, the alkyne moieties can be reduced (e.g., by Lindlar's catalyst) to form terminal alkene CNSL derivatives. A hydroboration-oxidation reaction can then be used to convert the alkene moieties into hydroxyl groups. Examples of these reactions are illustrated in FIGS. 4A and 4B. In other embodiments, the CNSL compounds can be reacted with a catalyst to form CNSL derivatives having saturated alkyl sidechains with terminal acetoxy groups. The terminal acetoxy groups can be removed to produce terminal polyol CNSL derivatives. An example of this is illustrated in FIG. 5.

Terminally-functionalized CNSL derivatives can optionally be reacted further to provide other reactive substituents (e.g., epoxy groups, propylene carbonate groups, vinyl groups, amine groups, carboxylic acid groups, aldehyde groups, acrylate groups, etc.). For example, epoxy resins can be formed by reacting terminal alkene CNSL derivatives with epichlorohydrin. In another example, a terminal vinyl CNSL derivative can be formed by attaching allyl substituents at phenolic hydroxyl groups of terminal alkene CNSL derivatives via a reaction with allyl chloride. Examples involving reactions to provide various terminal functional groups are discussed in greater detail with respect to FIG. 6.

The terminally-functionalized CNSL derivatives are then polymerized. This is illustrated at step 130. In some embodiments, the terminal polyol CNSL derivatives are reacted with appropriate co-reactants to form polyurethanes, polyesters, polyacrylates, or polycarbonates. Additionally, CNSL derivatives with terminal acetoxy groups formed at step 120 can be homopolymerized in a titanium-catalyzed polymerization reaction. In other embodiments, terminal epoxy CNSL derivatives can be catalytically homopolymerized or polymerized with co-monomers such as amines, acids, phenols, alcohols, and/or thiols. Examples of polymerization reactions are discussed in greater detail with respect to FIGS. 6-8. Applications of the CNSL-derived polymers can include flexible or rigid foams (e.g., for acoustic dampening or cushioning); plastics (e.g., for integrated circuit packages or other electronics hardware), textiles, insulation, and adhesives.

FIG. 2 is a chemical structure diagram illustrating examples of CNSL compounds 200, according to some embodiments of the present disclosure. The illustrated CNSL compounds 200 include anacardic acid 210, cardanol 220, cardol 230, and 2-methylcardol 240. These compounds 200 are distinguished from one another by the structures of their phenolic moieties (e.g., numbers of hydroxyl and/or methyl groups on the CNSL compound benzene rings). Each compound represents a mixture having phenolic moieties bound to C15 alkyl sidechains with different degrees of unsaturation.

In FIG. 2, the alkyl sidechains (L) are illustrated in descending order as a monoene sidechain (15:1), a diene sidechain (15:2), and a triene sidechain (15:3). Additionally, there can be small amounts (e.g., about 1-3%) of CNSL compounds with saturated alkyl sidechains in the mixture, as well as other components that do not substantially participate in the reactions illustrated herein (e.g., proteins, carbohydrates, minerals, etc.). These components are not illustrated herein, and are removed from the mixture in some embodiments.

The relative amounts of each CNSL compound 210, 220, 230, and/or 240 in a mixture can vary. For example, CNSL can contain about (~) 74-77% anacardic acid 210, ~15-20% cardol 230, ~1-10% cardanol 220, and ~2-3% 2-methylcardol 240. In another example, CNSL can contain ~80-90% anacardic acid 210, ~8-10% cardol 230, ~6% cardanol 220, and ~2% 2-methylcardol 240. In some embodiments, there is no 2-methylcardol 240 present in the mixture. For example, the CNSL can contain ~40% cardanol 220, ~30% cardol 230, and ~2% anacardic acid 210. Another mixture can contain ~60% anacardic acid 210, ~25% cardol 230, ~7% cardanol 220.

These amounts can optionally be adjusted by converting anacardic acid 210 into cardanol 220 (e.g., by heating, optionally in the presence of $Ca(OH)_2$) and/or isolating one or more of the CNSL compounds 200 (e.g., via column chromatography). The relative amounts of monoene, diene, and triene sidechains can also vary. For example, mixtures of the CNSL compounds 200 can contain ~50% trienes, ~30% dienes, and ~20% monoenes; ~40% trienes, ~20% dienes, and 36% monoenes; or ~36-50% trienes, ~18-32% dienes, and ~25-33% monoenes.

The degree of unsaturation and number of phenolic hydroxyl groups on the CNSL compounds 200 affect the properties of corresponding CNSL-derived polymers. This is because the carbon-carbon double bonds and hydroxyl groups participate in reactions to polymerize or attach additional functional groups to the CNSL derivatives. For example, a monoene cardanol 220 can be used to form a terminally-functionalized CNSL derivative with two reactive functional groups, while a triene cardol 230 can be used to form a terminally-functionalized CNSL derivative with five reactive functional groups.

Figure 6:
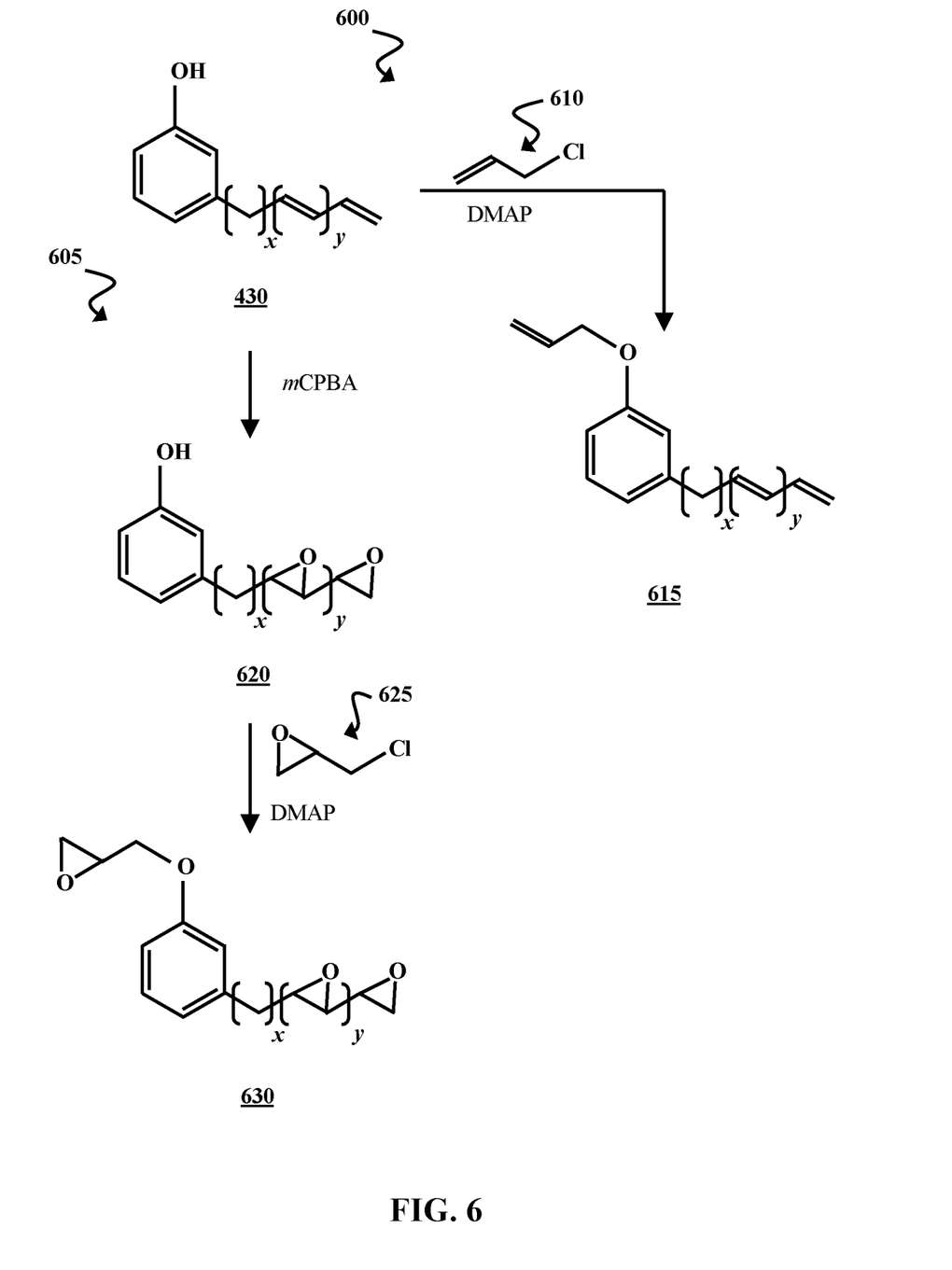
FIG. 6 is a chemical reaction diagram illustrating processes of forming terminal epoxy and terminal vinyl CNSL derivatives, according to some embodiments of the present disclosure.
Figure 7A:
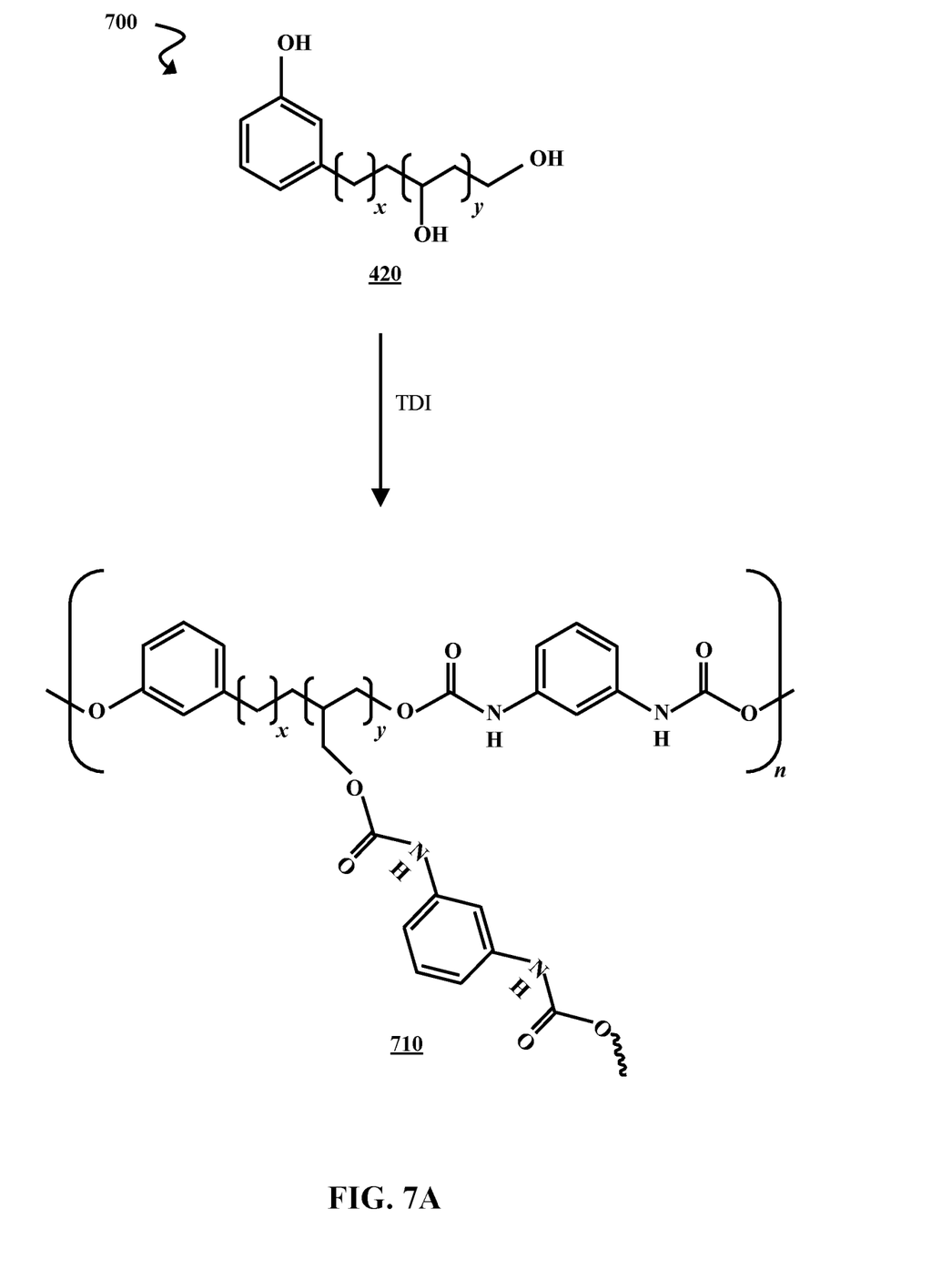
FIG. 7A is a chemical reaction diagram illustrating a process of forming CNSL-derived polyurethanes, according to some embodiments of the present disclosure. Polyurethanes can be formed by reacting
Figure 7B:
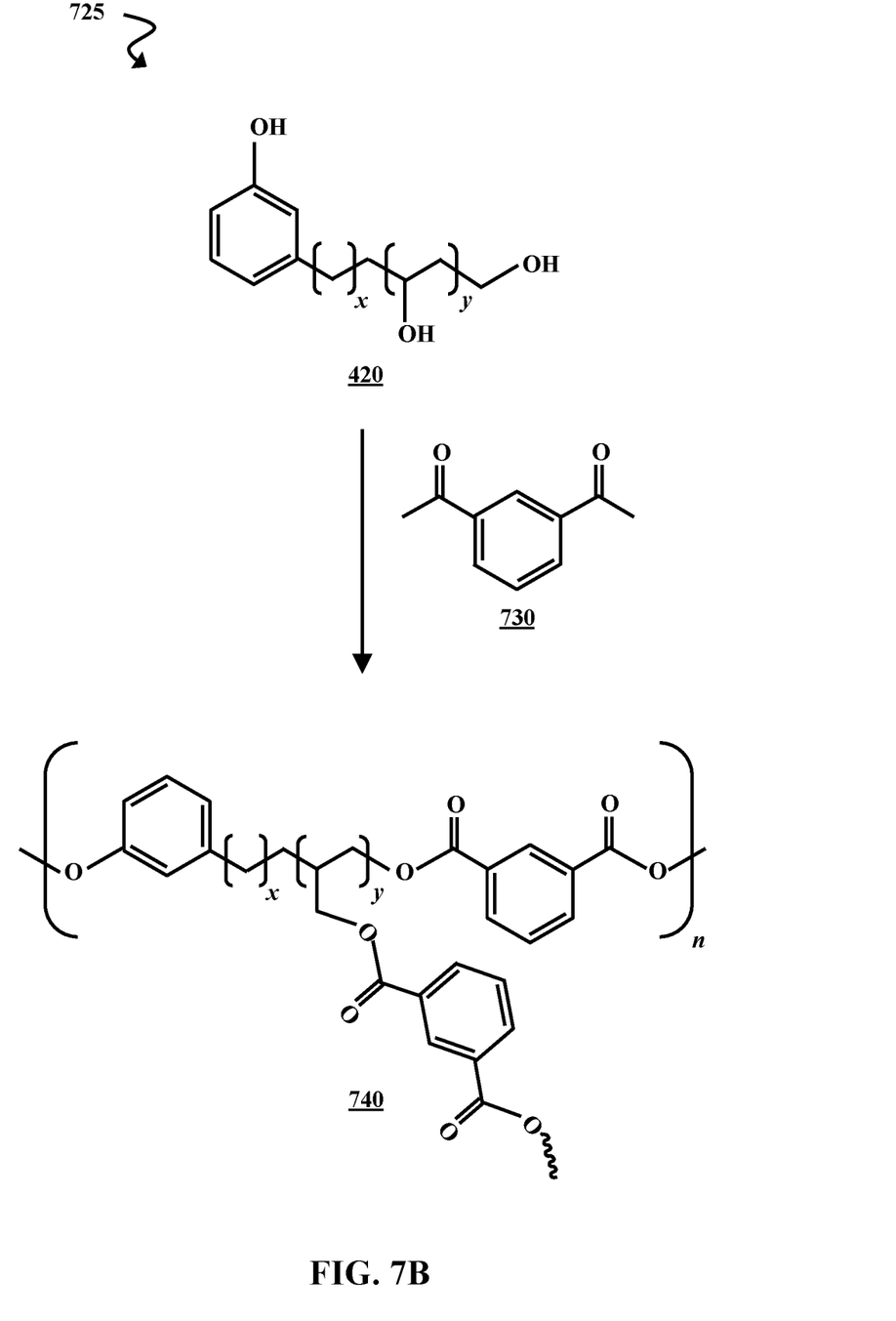
FIG. 7B is chemical reaction diagram illustrating a process of forming CNSL-derived polyesters, according to some embodiments of the present disclosure.
Figure 8:
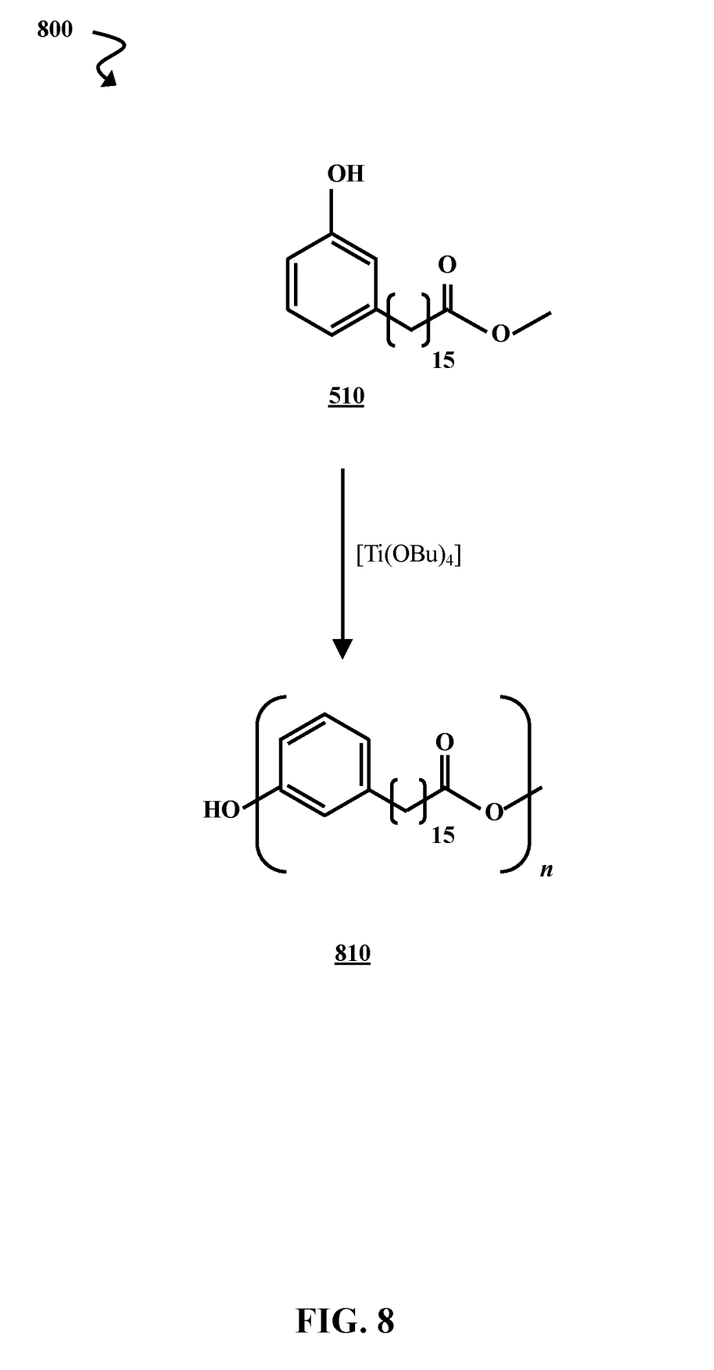
FIG. 8 is a chemical reaction diagram illustrating a process of forming CNSL-derived homopolymers, according to some embodiments of the present disclosure.

Polymerization of terminally-functionalized CNSL derivatives having more than two reactive functional groups forms a crosslinked polymer network because each reactive functional group can react to form covalent bonds. Polymerization of CNSL derivatives with five reactive functional groups will result in polymers having greater crosslinking density than polymerization of CNSL derivatives having fewer reactive functional groups. The density of crosslinking affects the mechanical properties of a polymer. For example, greater crosslinking density increases the rigidity of a polymer. Therefore, the type and relative amounts of CNSL compounds 200 used to form terminally-functionalized CNSL derivatives can be selected based on the desired properties of the resulting polymers. Examples of CNSL-derived polymers that can have varying degrees of crosslinking are illustrated in FIGS. 6-8.

FIG. 3 is a chemical reaction diagram illustrating a process 300 of forming terminal alkyne CNSL derivatives, according to some embodiments of the present disclosure. A mixture of CNSL compounds 310 is prepared. For simplicity, the CNSL compounds 310 are illustrated as cardanol alone. However, the CNSL compounds 310 can optionally include any of the CNSL compounds 200 illustrated in FIG. 2. Further, the CNSL compounds 310 can be present in any relative amounts, such as the amounts initially present in CNSL obtained at step 110 of process 100 (FIG. 1) or amounts adjusted by separation and/or conversion of anacardic acid 210 to cardanol 220. It should also be noted that in FIGS. 3-4B the monoene alkyl sidechain is illustrated as being bound to the phenol moiety while, for simplicity, the diene and triene sidechains are illustrated with a dashed line representing the phenol bond location.

The first step in process 300 involves oxidation of sidechain alkene moieties in the CNSL compounds 310 to alkyne moieties via a double elimination reaction. The CNSL compounds 310 are reacted with bromine ($Br_2$) to form vicinal halides (not shown). In some embodiments, chlorine or another halide is used instead of $Br_2$. Sodium hydroxide (NaOH) or another base (e.g., sodium amide ($NaNH_2$), sodium ethanethiolate ($CH_3CH_2SNa$), sodium ethoxide ($CH_3CH_2ONa$), etc.) is added to the reaction mixture, resulting in an elimination reaction that produces the alkyne CNSL derivatives 320.

An alkyne zipper reaction is then carried out in order to isomerize the alkyne CNSL derivatives 320 to form terminal alkyne CNSL derivatives 330. A solution of a base in its conjugate acid (potassium 3-aminopropylamide (KAPA)/1, 3-diaminopropane (APA)) is added to the alkyne CNSL derivatives 320. In some embodiments, at least one equivalent of KAPA/APA is added to the alkyne CNSL derivatives 320. However, a catalytic amount of KAPA/APA can be used in other embodiments (e.g., about 0.01-1% of the total weight of the reactants). Additionally, KAPA/APA can be replaced by other strong base/conjugate acid mixtures in some embodiments. For example, approximately one or more equivalents of dimsyl sodium (NaDMSO)/dimethylsulfoxide (DMSO) or $NaNH_2$/liquid ammonia ($NH_3$) can be used. The reaction is then acid ($H^+$)-quenched by addition of water and/or a weak acid. This yields the terminal alkyne CNSL derivatives 330.

FIG. 4A is a chemical reaction diagram illustrating a process 400 of forming terminal polyol CNSL derivatives, according to some embodiments of the present disclosure. The terminal alkyne derivatives 330 formed in process 300 can be combined with borane ($BH_3$), optionally in an organic solvent such as ether. However, any appropriate hydroboration reagent can be used. For example, $BH_3$ can be replaced by bis-(3-methylbutan-2-yl)boron (disiamylborane), 9-borabicyclo[3.3.1]nonane (9-BBN), or catecholborane (1,3,2-benzodioxaborole). Hydrogen peroxide ($H_2O_2$) and NaOH are then added to the reaction mixture. This results in formation of terminal carbonyl CNSL derivatives 410. The terminal carbonyl derivatives 410 are reacted with a reducing agent, sodium borohydride ($NaBH_4$), in diethyl ether ($Et_2O$) to form the terminal polyol CNSL derivatives 420.

FIG. 4B is a chemical reaction diagram illustrating a second process 425 of forming terminal polyol CNSL derivatives, according to some embodiments of the present disclosure. The terminal alkyne CNSL derivatives 330 (FIG. 3) are reduced by hydrogen ($H_2$) gas and a catalyst, yielding terminal alkene CNSL derivatives 430. In some embodiments, the catalyst is Lindlar's catalyst, which is a palladium on calcium carbonate ($Pd/CaCO_3$) catalyst "poisoned" with traces of lead, sulfur, and/or quinoline. However, other catalysts capable of reducing alkynes without reducing alkenes can also be used (e.g., nickel borides (Ni—B) or palladium on barium sulfate ($Pd/BaSO_4$) catalysts). The terminal alkene CNSL derivatives 430 are then converted into the terminal hydroxyl CNSL derivatives 420 in a hydroboration-oxidation reaction. This reaction can be carried out using techniques and reactants substantially similar to those of the hydroboration-oxidation in process 400 (FIG. 4A).

FIG. 5 is a chemical reaction diagram illustrating a third process 500 of forming terminal polyol CNSL derivatives, according to some embodiments of the present disclosure. Process 500 begins with selective hydrogenation of the CNSL compounds 310 illustrated in FIG. 3. The CNSL compounds 310 are reacted with palladium on alumina ($Pd/Al_2O_3$) in the presence of $H_2$ gas, resulting in a reaction mixture (not shown) where all of the CNSL compounds 310 are monoenes. This is followed by an isomerizing alkoxy-carbonylation reaction, which involves a catalyzed reaction between the monoene CNSL compounds 310 and methanol (MeOH) under about 2,000 kPa (20 bar) carbon monoxide (CO). In some embodiments, pyridine is added to the reaction in order to suppress acid-promoted transesterification. Additionally, MeOH can be replaced by another alcohol (e.g., ethanol or benzyl alcohol) in some embodiments. The reaction is catalyzed by a palladium (Pd) catalyst [(dtbpx)Pd(OTf)$_2$], where dtbpx is 1,2-bis-{di-tert-butylphosphino)methyl}benzene and OTf is triflate ($CF_3SO_3^-$).

The reaction mixture is maintained at approximately 90° C. for about 20 hours. This results in the formation of terminal ester CNSL derivatives 510 and saturated side-products 520. As in FIGS. 3-4B, the phenolic group corresponding to cardanol 220 is illustrated. However, any mixture of the CNSL compounds 310 can be used as starting materials, resulting in terminal ester CNSL derivatives 510 with corresponding phenol groups. The terminal ester groups on the terminal ester CNSL derivatives 510 are then reduced by lithium aluminum hydride ($LiAlH_4$) in tetrahydrofuran (THF). This reaction results in terminal polyol CNSL derivatives 530, which are separated from the saturated CNSL compound side-products 520 (e.g., by column chromatography).

In FIGS. 6-8, the CNSL derivative C15 alkyl sidechains are illustrated as having phenolic groups corresponding to cardanol 220, variable numbers (x) of methylene spacer (—$CH_2$—) groups, and variable numbers (y) of moieties containing a reactive functional group. The identities of x and y correspond to the CNSL compounds 200 (illustrated in FIG. 2) used to form each derivative. There can be CNSL derivatives where x=13 and y=0, where x=11 and y=1, and/or where x=9 and y=2. Additionally, the phenolic groups on the CNSL derivatives correspond to the phenolic groups on the mixture of starting CNSL compounds 310.

FIG. 6 is a chemical reaction diagram illustrating processes 600 and 605 of forming terminal epoxy and terminal vinyl CNSL derivatives, according to some embodiments of the present disclosure. In process 600, terminal alkene CNSL derivatives 430 (FIG. 4B) are reacted with allyl chloride 610 and 4-dimethylaminopyridine (DMAP), though catalytic triethylamine can optionally be used instead of DMAP. This reaction attaches allyl groups at the phenolic hydroxyl groups on the terminal alkene CNSL derivatives 430, resulting in derivatives 615 having terminal vinyl (—CH=$CH_2$) moieties (terminal vinyl CNSL derivatives 615).

In process 605, the terminal alkene CNSL derivatives 430 are reacted with meta-chloroperoxybenzoic acid (mCPBA), which converts the sidechain double bonds into epoxy groups, resulting in epoxy sidechain CNSL derivatives 620. However, in some embodiments, the epoxidation can occur via a low-temperature reaction with peracetic acid or hydrogen peroxide. Epichlorohydrin 625 and DMAP can then be reacted with the epoxy sidechain CNSL derivatives 620. This reaction attaches substituents having epoxy groups at the phenolic hydroxyl groups on the terminal alkene CNSL derivatives 430, resulting in compounds 630 referred to herein as "terminal epoxy CNSL derivatives 630". In some embodiments, the terminal epoxy CNSL derivatives 630 are further reacted with lithium bromide (LiBr) and carbon dioxide ($CO_2$) in order to convert the epoxy groups into propylene carbonate groups. The resulting terminal propylene carbonate CNSL derivatives are not illustrated herein.

The terminally-functionalized CNSL derivatives formed in processes 600 and 605 can be polymerized using a variety of techniques and, optionally, co-monomers. In some embodiments, these polymers have number average molecular weights ($M_N$) between about 700 g/mol and 25,000 g/mol (e.g., about 2,000 g/mol, about 5,000 g/mol, about 15,000 g/mol, etc.). However, polymerization of CNSL derivatives formed in process 600 or 605 can also result in polymers where $M_N$ is below 700 g/mol (e.g., about 250-450 g/mol) or above 25,000 g/mol (e.g., about 50,000-100,000 g/mol). Various additives can also be incorporated into these polymers. Examples of additives are discussed in greater detail below.

Reactions to polymerize the terminal vinyl and terminal epoxy CNSL derivatives 615 and 630, respectively, are not illustrated in FIG. 6. However, in some embodiments the terminal vinyl CNSL derivatives 615 are polymerized by a radical initiator (e.g., benzoyl peroxide or 2,2'-azo-bis-isobutyrylnitrile (AIBN)), an anionic initiator (e.g., butyl lithium), or a cationic initiator (e.g., aluminum trichloride ($AlCl_3$)). Metallocene polymerization or Zeigler-Natta catalysis can also be used to polymerize the terminal vinyl CNSL derivatives 615.

The terminal epoxy CNSL derivatives 630 can be cured by various catalysts (e.g., tertiary amines, Lewis acids, boron trifluoride ($BF_3$)-amine complexes), hardeners (e.g., aliphatic amines, aromatic amines, carboxylic anhydrides, etc.), and/or accelerators (e.g., benzyl dimethyl amine (BDMA), imidazoles, boron trichloride ($BCl_3$)-amine complexes, tertiary amines, boric acid esters, Lewis acids, organic metal compounds, organic metal salts, etc.). Additional examples of epoxy curing agents that can be used can include secondary amines, cycloaliphatic amines, amidoamines, polyamides, phenalkamines, o-tolyl biguanide, phenol formaldehydes, heterocyclic amines, polymercaptan, polysulfide resins, dicyandiamide, organic acid hydrazides, light-curing agents, ultraviolet (UV)-curing agents, etc. Additionally, in instances where propylene carbonate CNSL derivatives are produced following process 605, polymers such as polyhydroxyurethanes (PHUs) and polycarbonates can be formed.

FIG. 7A is a chemical reaction diagram illustrating a process 700 of forming CNSL-derived polyurethanes, according to some embodiments of the present disclosure. Terminal polyol CNSL derivatives 420 (FIG. 4A) are reacted with toluene diisocyanate (TDI) to form a CNSL-derived polyurethane 710. TDI can refer to 2,4-toluene diisocyanate, 2,6-diisocyanate, or a mixture thereof. However, isocyanates other than TDI can be used to form a variety of polyurethanes. These isocyanates can include aliphatic diisocyanates such as pentamethylene diisocyanate (PDI), hexamethylene diisocyanate (HDI), methylene dicyclohexyl diisocyanate (MDI), hydrogenated MDI (HMDI), and isophorone diisocyanate (IPDI); aliphatic polyisocyanates such as HDI trimer, HDI biuret, HDI uretdione, and IPDI trimer; and methylenediphenyl diisocyanate. Further, CNSL-derived polyurethanes 710 are formed using the terminal polyol CNSL derivatives 530 of process 500 (FIG. 5) in some embodiments.

The CNSL-derived polyurethane 710 can have any appropriate number (n) of repeat units. For example, n can be an integer between 1 and 1,000,000 (e.g., about 1-25,000, about 500-25,000, about 1,000-25,000, about 2,000-25,000, about 5,000-25,000, about 25,000-50,000, about 50,000-500,000, etc.). This is discussed in greater detail below. The polyurethane 710 can have a linear structure when the CNSL derivatives 420 are diols. However, crosslinked network structures can be formed when the polymerization reaction includes at least one CNSL derivative 420 having more than two hydroxyl groups. A sidechain crosslinker on the CNSL-derived polyurethane 710 is illustrated with a wavy line representing its connection to the rest of the polymer network.

A variety of additives can be used in forming the CNSL-derived polyurethane 710. These can include catalysts (e.g., benzyldimethylamine (B DMA), N,N-dimethylcyclohexylamine (DMCHA), N,N-dimethylethanolamine (DMEA), N,N,N',N'',N''-pentamethyldiethylenetriamine (TMDETA), 1,4-diazabicyclo[2.2.2]octane (DABCO), DABCO in dipropylene glycol, N,N,N-tris(3-dimethylaminopropyl)amine, bis-(2-dimethylaminoethyl)ether, N,N,N',N'',N''-pentamethyldipropylenetriamine (PMDPTA), etc.), aldehyde scavengers, cell openers, density modifiers, blowing agents (e.g., water, optionally in combination with liquid $CO_2$), silicone surfactants, etc. However, any appropriate additives can be used. Additional examples of additives that can be incorporated into CNSL-derived polyurethane 710 are discussed in greater detail below.

FIG. 7B is a chemical reaction diagram illustrating a process 725 of forming CNSL-derived polyesters, according to some embodiments of the present disclosure. In process 725, terminal polyol CNSL derivatives 420 (FIG. 4B) are reacted with dimethyl isophthalate 730 to form a CNSL-derived polyester 740. The CNSL-derived polyester 740 can have any appropriate number (n) of repeat units. This is discussed in greater detail below. The CNSL-derived polyester 740 can have a linear or crosslinked network structure. As in FIG. 7A, an example of a crosslinking bond is represented by a wavy line. Additives such as crosslinking initiators (e.g., benzoyl peroxide or methyl ethyl ketone peroxide (MEKP)) can optionally be used in process 725. Additional examples of additives that can be incorporated into the CNSL-derived polyester 740 are discussed in greater detail below.

The CNSL-derived polyester 740 can also be formed using co-reactants other than dimethyl isophthalate 730. For example, dimethyl isophthalate 730 can be replaced by diethyl isophthalate, isophthaloyl chloride, or any appropriate organic compound having at least two reactive functional groups such as esters, carboxylic acids, or acyl chlorides (e.g., dimethyl maleate, maleic acid, phthalic acid, isophthalic acid, terephthalic acid, fumaryl chloride, etc.). Further, CNSL-derived polyester 740 can be formed using the terminal polyol CNSL derivatives 530 of process 500 (FIG. 5) in some embodiments.

FIG. 8 is a chemical reaction diagram illustrating a process 800 of forming CNSL-derived homopolymers, according to some embodiments of the present disclosure. The terminal ester CNSL derivatives 510 (FIG. 5) are polymerized in a titanium-catalyzed polycondensation reaction, resulting in the CNSL-derived homopolymer 810. In process 800, the titanium catalyst is titanium(IV) butoxide ([Ti(OBu)$_4$]). However, other titanium-based polycondensation catalysts can be used as well, such as titanium(IV) isopropoxide, titanium(IV) ethoxide, titanium(IV) 2-ethylhexoxide, titanium(IV) (triethanolaminato)isopropoxide, acetal triisopropyl titanate, hexyleneglycol titanate, tetraisooctyl titanate, tetraethylhexyltitanate, titanium tetramethylate, titanium glycolate, titanium tetrapropylate, or phosphinic acid titanates combined with phosphoric acid. However, any appropriate polycondensation catalyst can be used instead of or in addition to a titanium-based catalyst. For example, antimony- or germanium-based catalysts can be used. Additional examples of catalysts that may be used can include catalysts based on tin, aluminum, samarium, iron, molybdenum, tungsten, magnesium/potassium/phosphorus, and zirconium/silicon/cobalt.

Any appropriate polymer additives known to a person of ordinary skill in the art can also be incorporated into the CNSL-derived polymers described herein (e.g., polymers illustrated in FIGS. 6-8). For example, at least one blowing agent can be added to make CNSL-derived polymer foams. Examples of blowing agents that can be used can include water/isocyanates (for polyurethane foams), liquids having low boiling points (e.g., pentane, isopentane, cyclopentane, or liquid $CO_2$), porous or hollow particles (e.g., glass, epoxide, or poly(vinylidene chloride) spheres/shells; fly ash; vermiculite; etc.), azodicarbonamide (for vinyls), and hydrazines (for thermoplastics and elastomers). Foams can also be mechanically generated (e.g., by whisking or injection of gas).

Additional examples of additives that can be incorporated into the CNSL-derived polymers can include surfactants (e.g., polydimethylsiloxane-polyoxyalkylene block copolymers, silicone oils, nonylphenol ethoxylates, etc.), fillers (e.g., chalk, fiberglass, plaster, glass microspheres, talc, marble dust, sand, ground limestone, bronze powder, etc.), chain extenders (e.g., chlorinated hydrocarbons), flame-retardants (e.g., phosphorus-based or halogenated flame retardants), smoke suppressants (e.g., ammonium octamolybdate or other molybdate ($MoO_4^{2-}$)-based compounds, trialkyl phosphate, ferrocene, tin compounds, etc.), plasticizers (e.g., esters of benzene-1,2-dicarboxylic acid, diisooctyl phthalate, organophosphates, glycols/polyethers, polymeric plasticizers, adipates, sebacates, maleates, trimellitates, di- or tricarboxylic ester-based plasticizers, etc.), pigments (titanium dioxide, iron oxide yellow, nickel titanates, chrome titanates, chrome yellow, cadmium yellow, iron oxide brown, iron oxide red, cadmium red, iron/manganese mixed metal oxide black, iron oxide black, carbon black, mixed metal oxide blue, chrome oxide green, phthalocyanine blue, phthalocyanine green, perylene red, quinacridone red, monoazo yellow, isoindoline yellow, monoaryide yellow, etc.), thinners (e.g., acetone or styrene), stretching aids (e.g., titanium(IV) dioxide ($TiO_2$) or barium sulfate ($BaSO_4$)), melt viscosity modifiers (e.g., pentaerythrite), optical brighteners (e.g., 4,4'-diamino-2,2'-stilbenedisulfonic acid or other stilbenes), antimicrobial agents (e.g., silver metal or silver ions fixed to a ceramic carrier), and stabilizers (e.g., mixtures of metal octadecanoates; lead carbonate (<1%); phosphoric acid, phosphorous acid, or esters thereof; etc.). The additives can be incorporated at any appropriate step in the polymerization process (e.g., during polymerization, foaming, mixing, extrusion, etc.).

Further, the CNSL-derived polymers described herein can have any appropriate number (n) of repeat units. For example, n can be an integer between 1 and 1,000,000 (e.g., about 1-25,000, about 500-25,000, about 1,000-25,000, about 2,000-25,000, about 5,000-25,000, about 25,000-50,000, about 50,000-500,000, etc.). The number of repeat units depends upon the quantities of monomers and co-reactants (e.g., initiators and/or additives), reaction time, and other reaction conditions. These parameters can be selected based on the amount of polymer to be prepared and/or intended polymer properties. Copolymers (e.g., alternating, random, or block copolymers) formed from the disclosed CNSL derivatives include at least one additional repeat unit having a different structure than the n repeat units, though examples of these are not illustrated herein. Depending upon the presence of crosslinking co-reactants and the number and identity of reactive functional groups on the terminally-functionalized CNSL derivatives and/or co-monomers, the CNSL-derived polymers can have linear or non-linear (e.g., branched, network, or cyclic) structures.

The compounds described herein can contain one or more chiral centers. Unless otherwise noted, the disclosed structures cover all stereoisomers, conformers, rotamers, isomers, and enantiomers of the represented compounds. Further, polymers or other materials containing the disclosed compounds can include racemic forms of the compounds in addition to individual stereoisomers, as well as mixtures containing any of these. Substituents on the terminally-functionalized CNSL derivatives and/or polymers described herein may participate in additional chemical reactions, transformations, or interactions, which can include synthesis, decomposition, single and/or double replacement, oxidation/reduction, acid/base, nucleophilic, electrophilic and radical substitutions, addition/elimination reactions, and polymerization reactions.

Where isomers of a named alkyl, alkenyl, alkoxy, aryl, or other functional group exist (e.g., n-butyl, iso-butyl, sec-butyl, and tert-butyl), reference to a member of the group without specifying a particular isomer (e.g., butyl) is intended to include all isomers in the family (e.g., n-butyl, iso-butyl, sec-butyl, and tert-butyl). Further, unless specified otherwise, reference to one member of the group (e.g., n-butyl) includes the remaining isomers in the family (e.g., iso-butyl, sec-butyl, and ten-butyl).

Unless otherwise noted, chemical reactions are performed at ambient conditions or under slight heating with no special atmosphere or head space, and may be performed using standard organic solvents to manage mix properties such as viscosity and flow index. Standard procedures for quenching reactions, solvent removal, and purification are performed. Room temperature is between about 15° C. and 25° C. unless otherwise indicated. Ranges (e.g., time, concentration, temperature, etc.) indicated herein include both endpoints and all numbers between the endpoints. Unless specified otherwise, the use of "about," "approximately," or a tilde (~) in connection to a range applies to both ends of the range (e.g., "approximately 1 g-5 g" should be interpreted as "approximately 1 g-approximately 5 g"). Unless otherwise indicated, modifying terms such as "about," "approximately," and "~" indicate +/−10% of a recited value, range of values, or endpoints of one or more ranges of values.

The processes discussed herein and their accompanying drawings are not to be construed as limiting. One skilled in the art would recognize that a variety of techniques may be used that vary in conditions, components, methods, etc., which ultimately generate terminally-functionalized CNSL derivatives and CNSL-derived polymers. In addition, the conditions can optionally be changed over the course of a process. Further, in some embodiments processes can be added, omitted, or carried out in alternate orders, while still remaining within the scope of the disclosure, as will be understood by a person of ordinary skill in the art. It should also be noted that processes can be carried out by a single entity, or by multiple entities. For example, a first entity may produce the terminally-functionalized CNSL derivatives and a second entity may produce the CNSL-derived polymers.

What is claimed is:
1. A compound having the structure:

wherein R, R', R", Q, and Q' are hydroxyl groups.

2. A method, comprising:
obtaining a cashew nutshell liquid (CNSL) compound;
converting sidechain alkene moieties on the CNSL compound to alkyne moieties to form an alkyne CNSL derivative;
reacting the alkyne CNSL derivative with a base to form a terminal alkyne CNSL derivative;
hydroxylating the terminal alkyne CNSL derivative to form a terminal polyol CNSL derivative; and
polymerizing the terminal polyol CNSL derivative.

3. The method of claim 2, wherein the polymerizing comprises forming a polyurethane.

4. The method of claim 3, wherein the forming the polyurethane comprises reacting the terminal polyol CNSL derivative with an isocyanate.

5. The method of claim 4, wherein the isocyanate is selected from the group consisting of toluene diisocyanate, pentamethylene diisocyanate (PDI), methylene dicyclohexyl diisocyanate (MDI), hydrogenated MDI, isophorone diisocyanate (IPDI), hexamethylene diisocyanate (HDI), HDI trimer, HDI biuret, HDI uretdione, and IPDI trimer.

6. The method of claim 2, wherein the polymerizing comprises reacting the terminal polyol CNSL derivative with a diisocyanate.

7. The method of claim 2, wherein the polymerizing comprises adding a blowing agent.

8. The method of claim 2, wherein the polymerizing comprises forming a mixture, the mixture comprising:
the terminal polyol CNSL derivative; and
at least one monomer from a non-CNSL source.

9. The method of claim 8, wherein the at least one monomer is a petrochemical-derived polyol.

10. An article of manufacture comprising a polymer, the polymer comprising:
a number (n) of repeat units derived from a terminally-functionalized cashew nutshell liquid (CNSL) derivative having the structure:

wherein R, R', R", Q, and Q' are hydroxyl groups.

11. The article of manufacture of claim 10, wherein the polymer is a polyurethane.

12. The article of manufacture of claim 10, wherein the polymer is a foam.

13. The article of manufacture of claim 10, wherein the polymer is a polyester.

14. The article of manufacture of claim 10, wherein at least 5% by weight of the polymer is derived from the CNSL derivative.

* * * * *